United States Patent
Bernabei

(10) Patent No.: US 6,269,271 B1
(45) Date of Patent: Jul. 31, 2001

(54) METHOD AND APPARATUS FOR SKIN BROWN SPOT REMOVAL

(75) Inventor: Gian Franco Bernabei, Florence (IT)

(73) Assignee: Mattioli Engineering Ltd. (GB)

( * ) Notice: Subject to any disclaimer, the term of this patent is extended or adjusted under 35 U.S.C. 154(b) by 0 days.

(21) Appl. No.: 09/361,407

(22) Filed: Jul. 27, 1999

(51) Int. Cl.$^7$ ....................................................... A61F 7/00
(52) U.S. Cl. ................................. 607/99; 607/101; 607/98
(58) Field of Search ............................... 607/96, 98–101, 607/149–150; 606/41, 45, 49, 50

(56) References Cited

U.S. PATENT DOCUMENTS

| | | | |
|---|---|---|---|
| 5,746,746 | 5/1998 | Garito et al. . | |
| 5,868,744 | * 2/1999 | Willmen | 606/50 |
| 5,938,657 | * 8/1999 | Assa et al. | 606/9 |
| 6,063,085 | * 5/2000 | Tay et al. | 606/50 |
| 6,104,959 | * 8/2000 | Spertell | 607/101 |
| 6,117,109 | 9/2000 | Eggers et al. . | |
| 6,139,545 | * 10/2000 | Utley et al. | 606/34 |

OTHER PUBLICATIONS

Castillo, G. D., "Procedures Laser Skin Surgery", Cosmetic Plastic Surgery, Web article updated 10/98.*

* cited by examiner

*Primary Examiner*—Roy Gibson
(74) *Attorney, Agent, or Firm*—Foley & Lardner

(57) ABSTRACT

Radio frequency current pulses are applied to the skin in a controlled manner in order to heat selected volumes of skin, thereby inducing the removal of unwanted pigments from the skin. A probe provides the radio frequency current pulses to the skin, where the probe includes first and second metallic stripes, and where the probe is connected to two coaxial cables that are respectively connected to the first and second metallic stripes. The two coaxial cables are connected to a balanced/unbalanced transformer, which in turn is connected to a radio frequency generator that provides radio frequency pulses.

14 Claims, 1 Drawing Sheet

METHOD AND APPARATUS FOR SKIN BROWN SPOT REMOVAL

FIELD OF THE INVENTION

The present invention relates to a method and apparatus for skin brown spot removal, by using radio frequency pulses applied to the skin of a patient by a probe.

BACKGROUND OF THE INVENTION

It is well known that due to the aging process, some unwanted brown spots appears in the skin of the hands and arms. The color of the spots is mainly caused by a production of melanin.

Several methods have been tested in order to reduce the appearance of such spots, with these methods including the application of a laser at various wavelengths.

Some results have been achieved, but no method is at the present time is particularly effective and also does not have unwanted side effects.

When laser light reaches the skin, its intensity decreases exponentially in the skin. This means that the thermal energy that is delivered is higher in the first layer of the skin, and decreases exponentially as it penetrates lower into the lower layers of the skin. Moreover, the first corneum stratus (an upper skin layer) has a higher absorption than other portions of the skin. Such an energy profile is not suitable for uniform heating of a volume of skin due to the fact that in the superficial layers the reached temperature is too high and in other layers the temperature is not enough in order to trigger the desired brown spot reduction process.

The present invention is related to a different method of heating a portion of skin using radio frequency current pulses.

It is well known that an alternating voltage applied to a conductor generates a current on the external layer of the conductor, and the depth of current flow depends on the frequency and the resistance of the conductor (skin effect).

SUMMARY OF THE INVENTION

The present invention is directed to an apparatus and a treatment method for the removal of unwanted brown spots on the skin.

The present invention uses a pulsed radio frequency generator connected to a special probe for the coupling to the skin, and a water based substance for the enhancement of the effects. Such a combination is able to generate a controlled heating of a selected portion of the skin of a depth of 800 microns so that is possible to reach a temperature of 80 degrees Celsius, which triggers the decoloration of the melanin in the brown spots.

The method includes:
1) The application of radio frequency pulses at a frequency of 27 MHz on the skin over an area equal or less than 1 square centimeter for a time of less than 0.5 second and a power of less than 100 W.
2) An apparatus which includes the following to perform the preceding treatment:
   a) A radio frequency generator functioning in pulsed mode with powers and wavelengths in the ranges previously specified;
   b) a probe for applying the radio frequency current which permits concentration of heating in the selected volume of the skin;
   c) an impedance transformer in order to adapt the high impedance of the skin to the low impedance of the radio frequency generator.
3) The application on the skin of a water-based gel in order to decrease the impedance of the first layer of the skin and at the same time carry during the treatment additional substance that are usually employed for decreasing the appearance of the brown spots, such as cogic acid.

BRIEF DESCRIPTION OF THE DRAWINGS

The invention will become more fully apparent from the following detailed description when read in conjunction with the accompanying drawings with like reference numerals indicating corresponding parts throughout, and wherein.

DESCRIPTION OF THE PREFERRED EMBODIMENTS

According to the present invention, a water based gel is applied to the skin area to be treated. The effect of such a water based gel is to decrease the superficial electrical impedance to a value independent from the type and condition of the patient's skin.

Figure 2:
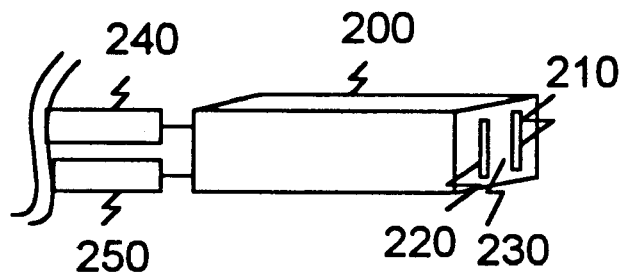
FIG. 2 is a plan view of a probe of the skin brown spot removal apparatus according to the invention.

A special probe that includes two electrodes is positioned on the gel that has been applied to the patient's skin. The probe has two metallic stripes, each having a dimension of 3 millimeter width×5 millimeter length and where the two metallic stripes are separated from each other by a distance of 5 millimeters, with an insulator such as plexiglass or plastic providing the separation. Other dimensions of the metallic stripes are possible while remaining within the scope of the invention, with those dimensions depending on the size of the brown spot to be removed. FIG. 2 shows a plan view of a probe 200 that includes a first metallic stripe 210, a second metallic stripe 220, and with insulator 230 provided between the first and second metallic stripes 210, 220. In the preferred embodiments, the entirety of the probe 200, except for the metallic stripes 210, 220 and any coaxial connection ports, is made of the insulator material.

Figure 3:
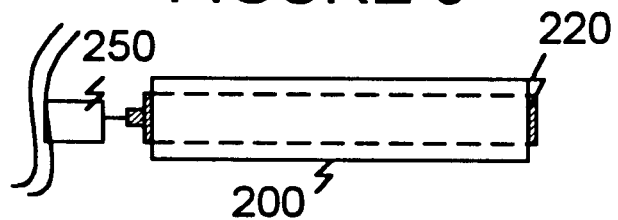
FIG. 3 is a side view of the probe according to the invention.
Figure 4:
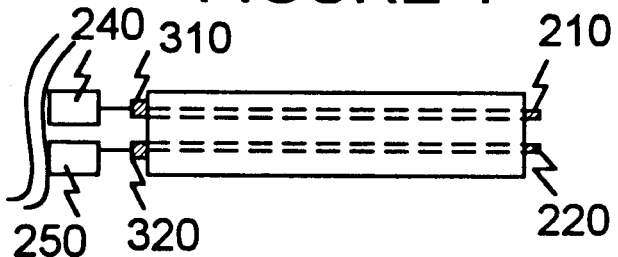
FIG. 4 is a top view of the probe according to the invention.

FIG. 3 shows a side view of the probe 200, in which a coaxial connection port 320 is provided on the probe 200 for connection to the coaxial cable 250. FIG. 4 shows an upper view of the probe 200, with both the coaxial connection port 320 and another coaxial connection port 310 of the probe 200 shown. The metallic stripes 210, 220 are mainly shown as dashed lines in FIG. 4 (except for the small portion extending out of the front side of the probe 200), since they are embedded within the probe 200.

As seen in FIGS. 2, 3 and 4, the two electrodes 210, 220 are respectively connected to two separate coaxial cables 240, 250 each having a length of 2.5 meters, and each acting as an impedance transformer. Of course, other cable lengths are possible while remaining within the scope of the invention. The cables 240, 250 are used in order to adapt the high impedance of the skin to the low impedance of the radio frequency generator that operates at a preferred frequency of 27 Mhz. The radio frequency generator may operate at other frequencies within the Mhz range while remaining within the scope of the invention.

Figure 1:
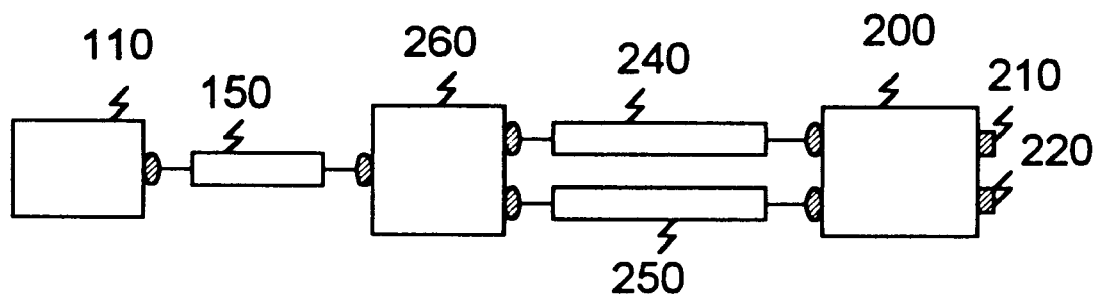
FIG. 1 is a block diagram of a skin brown spot removal apparatus according to the invention.

As shown in FIG. 1, the radio frequency generator 110 is connected to the two cables 240, 250 by way of a balanced-unbalanced transformer 260. The radio frequency generator 110 is preferably connected to the balanced-unbalanced transformer 260 by way of a coaxial cable 150.

The radio frequency generator 110 is capable of generating programmable pulses of selected time and peak power. Typical parameters are 100 millisecond time, 50 W peak power and 27 Mhz frequency. Other parameters are possible while remaining within the scope of the invention, with those parameters being selected based on the size of the probe and the desired penetration depth.

The radio frequency pulses generate an electromagnetic field between the two electrodes. The current density on the skin decrease sharply with the depth after 800 micron due to the skin effect. In such a way, the heating takes place only in a skin volume of about 5000×5000×800 microns. Moreover, the matching of the pulse duration with the thermal inertia of the skin and the thermal resistance enables the creation of an even (e.g., monotonic) increase of the temperature in the selected volume, thereby avoiding the problem of having the upper layers being too hot. The insulator between the two electrodes also has the function of keeping the first layer of the skin cool, thereby providing for a faster decrease of the skin temperature after a pulse has been applied (and before a next pulse is applied). The controlled heating of the area destroys the temperature-sensitive pigments without generating damage to the skin.

In a second embodiment, the effect is enhanced by the employment of substances that normally are used in order to decrease the appearance of the brown spot, such as cogic acid.

I claim:

1. A treatment system for removal of unwanted brown spots on skin, comprising:

a pulsed radio frequency generator with an operating power of between 1 and 100 W, and with an operating frequency of between 7 MHz and 52 MHz, and with an output pulsewidth of between 1 and 500 millisecond; and a probe that is connected to the pulsed radio frequency generator, the probe consisting of:
at least two electrodes each having a first end and a second end;
at least one coaxial connection port for connecting the probe to the pulse radio frequency generator, and
an insulator that is disposed between and around the at least two electrodes except for the respective first and second ends of the at least two electrodes, the insulator electrically separating the at least two electrodes from each other,
wherein the probe is applied to the skin in order to remove the unwanted brown spots from the skin.

2. A treatment system as in claim 1, wherein the probe includes no other elements besides the insulator, the at least two electrodes, and the at least one coaxial connection port.

3. A treatment system as in claim 1, wherein the first ends of the at least two electrodes are electrically connected to the at least one coaxial connection port at a first end of the probe, and wherein the second ends of the at least two electrodes extend out from a second end of the probe opposite the first end of the probe, so that the at least two electrodes are applied directly to the skin of the patient when the first end of the probe is applied to the skin of the patient.

4. A treatment system as in claim 1, wherein the insulator is one of plexiglass and plastic.

5. A treatment system as in claim 1, further comprising:
an balanced/unbalanced transformer that is provided between the pulsed radio frequency generator and the probe;
a first coaxial cable that provides rf coupling between the balanced/unbalanced transformer and the pulsed radio frequency generator;
a second coaxial cable that provides rf coupling between the balanced/unbalanced transformer and a first of the at least two electrodes of the probe; and
a third coaxial cable that provides rf coupling between the balanced/unbalanced transformer and a second of the at least two electrodes of the probe.

6. A treatment system as in claim 1, wherein the at least two electrodes of the probe are in direct contact with the skin so as to apply the at least one pulse directly to the skin.

7. A method for removing brown spots from a skin of a patient, comprising:

providing at least one pulse from an radio frequency generator that operates at between 1 and 100 W, a frequency of between 7 and 52 MHz, and a pulsewidth of between 1 and 500 milliseconds;

applying the at least one pulse to the skin of the patient by way of a probe connected to the radio frequency generator, wherein the probe includes at least two electrodes that extend from a proximal end to a distal portion of the probe, and an insulator portion disposed between and around the at least two electrodes except for a distal end surface and a proximal end surface of the at least two electrodes; and after the applying step, cooling off the skin by applying the insulator portion directly to the skin of the patient, so that the skin is cooled off prior to a next pulse being applied to the skin.

8. A method as in claim 7, further comprising:
before the applying step, providing a water based conductive substance on at least a portion of the skin of the patient where the probe is to be applied thereto.

9. A method as in claim 8, wherein the water based conductive substance includes cogic acid.

10. A method as in claim 7, wherein the probe is applied to an area of the skin of less than one square centimeter.

11. A method as in claim 7, wherein the insulator portion is one of plexiglass and plastic.

12. A method as in claim 7, wherein, during the applying step, the probe is in direct contact with the skin.

13. A method for removing brown spots from a skin of a patient, comprising:

providing at least one pulse from an radio frequency generator that operates at between 1 and 100 W, a frequency of between 7 and 52 MHz, and a pulsewidth of between 1 and 500 milliseconds;

applying the at least one pulse to the skin of the patient by way of a probe connected to the radio frequency generator, wherein the at least one pulse is applied to the skin of the patient, wherein the probe is in direct contact with the skin of the patient during the applying step.

14. A method as in claim 13, further comprising:
prior to the providing step, applying cogic acid to the skin of the patient so as to increase a conductivity of the skin of the patient.

\* \* \* \* \*